United States Patent
Vaillancourt et al.

(10) Patent No.: US 8,069,523 B2
(45) Date of Patent: Dec. 6, 2011

(54) SITE SCRUB BRUSH

(75) Inventors: Michael J. Vaillancourt, Chester, NJ (US); Marshall Kerr, Oceanside, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 12/584,740

(22) Filed: Sep. 11, 2009

(65) Prior Publication Data

US 2010/0083452 A1 Apr. 8, 2010

Related U.S. Application Data

(60) Provisional application No. 61/195,002, filed on Oct. 2, 2008.

(51) Int. Cl.
*B08B 9/00* (2006.01)
(52) U.S. Cl. ............... 15/104.94; 15/104.93; 15/160; 604/267
(58) Field of Classification Search ........... 15/104.04, 15/104.05, 104.92, 104.93, 160, 104.94; 604/265, 267
See application file for complete search history.

(56) References Cited

U.S. PATENT DOCUMENTS

| | | |
|---|---|---|
| 2,878,128 A | 3/1959 | Jorgenson |
| 3,396,727 A | 8/1968 | Mount |
| 3,450,129 A | 6/1969 | Brewer |
| 3,860,348 A * | 1/1975 | Doyle .............................. 401/6 |
| 3,915,806 A | 10/1975 | Horlach |
| 3,961,629 A | 6/1976 | Richter et al. |
| 4,340,052 A | 7/1982 | Dennehey et al. |
| 4,354,490 A | 10/1982 | Rogers |
| 4,417,890 A | 11/1983 | Dennehey et al. |
| 4,432,259 A | 2/1984 | Werth, Jr. |
| 4,432,764 A | 2/1984 | Lopez |
| 4,440,207 A | 4/1984 | Genatempo et al. |
| 4,551,146 A | 11/1985 | Rogers |
| 4,624,664 A | 11/1986 | Peluso et al. |
| 4,734,950 A | 4/1988 | Schenke et al. |
| 4,752,983 A | 6/1988 | Grieshaber |
| 4,830,674 A | 5/1989 | Kaufman |
| 4,862,549 A | 9/1989 | Criswell et al. |
| 4,872,235 A | 10/1989 | Nielsen |
| 4,886,388 A | 12/1989 | Gulker et al. |
| 4,893,956 A | 1/1990 | Wojcik et al. |
| 4,919,837 A | 4/1990 | Gluck |
| 4,989,733 A | 2/1991 | Patry |

(Continued)

FOREIGN PATENT DOCUMENTS

DE   10335794 A1   10/2005

(Continued)

OTHER PUBLICATIONS

EP08250832 filed Mar. 12, 2008 EP Search Report dated Aug. 15, 2008.

(Continued)

*Primary Examiner* — Shay Karls
(74) *Attorney, Agent, or Firm* — Rutan & Tucker, LLP

(57) ABSTRACT

The site scrub brush is made of a block of foam material, such as a semi-closed hydrophilic polyurethane medical grade foam, with a thin layer of sealing material, such as any plastic polymer which is non-permeable in nature, about the periphery and bottom. The brush is compressible under finger pressure to enhance the scrubbing action of the brush on the outer surfaces of a luer received by the brush.

16 Claims, 2 Drawing Sheets

U.S. PATENT DOCUMENTS

| | | |
|---|---|---|
| 5,049,139 A | 9/1991 | Gilchrist |
| 5,180,061 A | 1/1993 | Khan et al. |
| 5,195,957 A | 3/1993 | Tollini |
| 5,242,425 A | 9/1993 | White et al. |
| 5,274,874 A | 1/1994 | Cercone et al. |
| 5,308,406 A | 5/1994 | Wallock et al. |
| 5,330,235 A | 7/1994 | Wagner et al. |
| 5,368,049 A | 11/1994 | Raman et al. |
| 5,372,429 A | 12/1994 | Beaver, Jr. et al. |
| 5,471,706 A | 12/1995 | Wallock et al. |
| 5,536,258 A | 7/1996 | Folden |
| 5,554,135 A | 9/1996 | Menyhay |
| 5,719,113 A | 2/1998 | Fendler et al. |
| 5,722,537 A | 3/1998 | Sigler |
| 5,743,892 A | 4/1998 | Loh et al. |
| 5,763,412 A | 6/1998 | Khan et al. |
| 5,776,430 A | 7/1998 | Osborne et al. |
| 5,782,808 A | 7/1998 | Folden |
| 5,792,120 A | 8/1998 | Menyhay |
| 5,829,976 A | 11/1998 | Green |
| 5,830,488 A | 11/1998 | Suzuki et al. |
| 5,894,015 A | 4/1999 | Rechtin |
| 5,906,808 A | 5/1999 | Osborne et al. |
| 5,980,925 A | 11/1999 | Jampani et al. |
| 6,045,539 A | 4/2000 | Menyhay |
| 6,045,623 A | 4/2000 | Cannon |
| 6,086,275 A | 7/2000 | King |
| 6,096,701 A | 8/2000 | Mondin et al. |
| 6,108,847 A | 8/2000 | Cueman et al. |
| 6,110,292 A | 8/2000 | Jewett et al. |
| 6,116,468 A | 9/2000 | Nilson |
| 6,130,196 A | 10/2000 | Mondin et al. |
| 6,143,025 A | 11/2000 | Stobie et al. |
| 6,152,913 A | 11/2000 | Feith et al. |
| 6,250,315 B1 | 6/2001 | Ernster |
| 6,254,550 B1 | 7/2001 | McNamara et al. |
| 6,289,547 B1 | 9/2001 | Narula et al. |
| 6,299,520 B1 | 10/2001 | Cheyne, III |
| 6,357,947 B1 | 3/2002 | Mark |
| 6,387,865 B1 | 5/2002 | Mondin et al. |
| 6,387,866 B1 | 5/2002 | Mondin et al. |
| 6,395,697 B1 | 5/2002 | Cheung et al. |
| 6,432,213 B2 | 8/2002 | Wang et al. |
| 6,447,446 B1 | 9/2002 | Smith et al. |
| 6,472,356 B2 | 10/2002 | Narula et al. |
| 6,488,942 B1 | 12/2002 | Ingemann |
| 6,508,602 B1 | 1/2003 | Gruenbacher et al. |
| 6,564,415 B1 | 5/2003 | Katakura et al. |
| 6,589,212 B1 | 7/2003 | Navis |
| 6,617,294 B2 | 9/2003 | Narula et al. |
| 6,669,387 B2 | 12/2003 | Gruenbacher et al. |
| 6,708,363 B2 | 3/2004 | Larsen |
| 6,726,386 B1 | 4/2004 | Gruenbacher et al. |
| 6,745,425 B1 | 6/2004 | Tope |
| 6,821,043 B2 | 11/2004 | Teh |
| 6,855,678 B2 | 2/2005 | Whiteley |
| 6,911,025 B2 | 6/2005 | Miyahara |
| 6,991,527 B2 | 1/2006 | Linzell |
| 7,083,605 B2 | 8/2006 | Miyahara |
| 7,108,440 B1 | 9/2006 | Gruenbacher et al. |
| 7,163,914 B2 | 1/2007 | Gluck et al. |
| 7,179,007 B2 | 2/2007 | Wong et al. |
| 7,199,090 B2 | 4/2007 | Koivisto et al. |
| 7,282,186 B2 | 10/2007 | Lake, Jr. et al. |
| 7,338,927 B2 | 3/2008 | Shapiro |
| 7,452,349 B2 | 11/2008 | Miyahara |
| 7,488,757 B2 | 2/2009 | Hoang et al. |
| 7,513,957 B2 | 4/2009 | Condliff |
| 7,537,779 B2 | 5/2009 | Modak et al. |
| D596,308 S | 7/2009 | Fisher |
| 7,560,422 B2 | 7/2009 | Shapiro |
| D607,325 S | 1/2010 | Rogers et al. |
| 2001/0031221 A1 | 10/2001 | Wu et al. |
| 2001/0031721 A1 | 10/2001 | Webb et al. |
| 2001/0032659 A1 | 10/2001 | Wang et al. |
| 2002/0002984 A1 | 1/2002 | Loy |
| 2002/0022660 A1 | 2/2002 | Jampani et al. |
| 2002/0062147 A1 | 5/2002 | Yang |
| 2003/0019767 A1 | 1/2003 | Cabrera |
| 2003/0144647 A1 | 7/2003 | Miyahara |
| 2003/0147925 A1 | 8/2003 | Sawan et al. |
| 2003/0156884 A1 | 8/2003 | Teh |
| 2003/0164175 A1 | 9/2003 | Linzell |
| 2003/0211066 A1 | 11/2003 | Scholz et al. |
| 2003/0213501 A1 | 11/2003 | Thomson et al. |
| 2003/0217423 A1 | 11/2003 | Larsen |
| 2004/0052831 A1 | 3/2004 | Modak et al. |
| 2004/0111078 A1 | 6/2004 | Miyahara |
| 2004/0214785 A1 | 10/2004 | Dees et al. |
| 2004/0230162 A1 | 11/2004 | Tan |
| 2004/0237235 A1 | 12/2004 | Visioli et al. |
| 2004/0258560 A1 | 12/2004 | Lake et al. |
| 2005/0081888 A1 | 4/2005 | Pung et al. |
| 2005/0124970 A1 | 6/2005 | Kunin et al. |
| 2005/0171489 A1 | 8/2005 | Weaver et al. |
| 2005/0177964 A1 | 8/2005 | Cisneros |
| 2005/0201812 A1 | 9/2005 | Wong et al. |
| 2005/0214185 A1 | 9/2005 | Castaneda |
| 2005/0215461 A1 | 9/2005 | Gluck et al. |
| 2005/0222542 A1 | 10/2005 | Burkholz et al. |
| 2005/0241088 A1 | 11/2005 | Brunner et al. |
| 2005/0241089 A1 | 11/2005 | Brunner et al. |
| 2005/0282727 A1 | 12/2005 | Shapiro |
| 2006/0003082 A1 | 1/2006 | Marumo et al. |
| 2006/0030827 A1 | 2/2006 | Raulerson et al. |
| 2006/0048313 A1* | 3/2006 | Yamaki .......................... 15/21.1 |
| 2006/0102200 A1 | 5/2006 | Esquenet et al. |
| 2006/0189961 A1 | 8/2006 | Miyahara |
| 2006/0281663 A1 | 12/2006 | Asmus |
| 2007/0033753 A1 | 2/2007 | Kritzler |
| 2007/0065388 A1 | 3/2007 | Miyamoto et al. |
| 2007/0112333 A1 | 5/2007 | Hoang et al. |
| 2007/0130707 A1 | 6/2007 | Cohen et al. |
| 2007/0157408 A1 | 7/2007 | Bargiel et al. |
| 2007/0225660 A1* | 9/2007 | Lynn ............................ 604/265 |
| 2007/0266509 A1 | 11/2007 | Kohlruss et al. |
| 2007/0277852 A1 | 12/2007 | Condliff |
| 2007/0282280 A1 | 12/2007 | Tennican |
| 2008/0011310 A1 | 1/2008 | Anderson et al. |
| 2008/0014224 A1 | 1/2008 | Boyd et al. |
| 2008/0019889 A1 | 1/2008 | Rogers et al. |
| 2008/0033371 A1 | 2/2008 | Updegraff et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0098543 A1 | 5/2008 | Esquenet et al. |
| 2008/0103210 A1 | 5/2008 | Shapiro |
| 2008/0132880 A1 | 6/2008 | Buchman |
| 2008/0137969 A1 | 6/2008 | Rueckert et al. |
| 2008/0138438 A1 | 6/2008 | Taylor et al. |
| 2008/0147047 A1 | 6/2008 | Davis et al. |
| 2008/0152894 A1 | 6/2008 | Beihoffer et al. |
| 2008/0172007 A1 | 7/2008 | Bousquet |
| 2008/0177250 A1 | 7/2008 | Howlett et al. |
| 2008/0187460 A1 | 8/2008 | Utterberg et al. |
| 2008/0194994 A1 | 8/2008 | Bown et al. |
| 2008/0235888 A1 | 10/2008 | Vaillancourt et al. |
| 2009/0028750 A1 | 1/2009 | Ryan |
| 2009/0062766 A1 | 3/2009 | Howlett et al. |
| 2009/0099529 A1 | 4/2009 | Anderson et al. |
| 2009/0104281 A1 | 4/2009 | Taylor et al. |
| 2009/0117164 A1 | 5/2009 | Toreki et al. |
| 2009/0126134 A1 | 5/2009 | Whipple et al. |
| 2009/0137969 A1 | 5/2009 | Colantonio et al. |
| 2009/0143470 A1 | 6/2009 | Hoang et al. |
| 2009/0162301 A1 | 6/2009 | Tarrand |
| 2009/0165228 A1 | 7/2009 | Kilkenny et al. |
| 2009/0175759 A1 | 7/2009 | Davis et al. |
| 2009/0191249 A1 | 7/2009 | Adelakun |
| 2009/0205151 A1 | 8/2009 | Fisher et al. |
| 2009/0241991 A1 | 10/2009 | Vaillancourt et al. |
| 2010/0050351 A1 | 3/2010 | Colantonio et al. |
| 2010/0200017 A1 | 8/2010 | Kerr et al. |
| 2011/0030726 A1 | 2/2011 | Vaillancourt et al. |

FOREIGN PATENT DOCUMENTS

| | | |
|---|---|---|
| DE | 102005027982 A1 | 12/2006 |
| EP | 1977714 A1 | 10/2008 |
| JP | 2003319825 A | 11/2003 |
| JP | 2008094915 A | 4/2008 |
| WO | 9904623 A1 | 2/1999 |
| WO | 0015036 A1 | 3/2000 |
| WO | 2004018003 A1 | 3/2004 |
| WO | 2004084973 A2 | 10/2004 |
| WO | 2006019782 A2 | 2/2006 |
| WO | 2006062846 A2 | 6/2006 |
| WO | 2006138111 A1 | 12/2006 |
| WO | 2007084908 A2 | 7/2007 |
| WO | 2007097985 A2 | 8/2007 |
| WO | 2007137056 A2 | 11/2007 |
| WO | 2008100950 A2 | 8/2008 |
| WO | 2009123709 A2 | 10/2009 |
| WO | 2010039171 A1 | 4/2010 |
| WO | 2011022601 A1 | 2/2011 |

OTHER PUBLICATIONS

PCT/US2009/002011 filed Mar. 30, 2009 Search Report dated Jun. 1, 2009.
PCT/US2009/002011 filed Mar. 30, 2009 Written Opinion dated Jun. 1, 2009.
PCT/US2009/005120 filed Sep. 14, 2009 Search Report dated Jul. 1, 2010.
PCT/US2010/029641 filed Apr. 1, 2010 Search Report dated Jul. 1, 2010.
PCT/US2010/029641 filed Apr. 1, 2010 Written Opinion dated Jul. 1, 2010.
U.S. Appl. No. 60/832,437, filed Jul. 21, 2006 entitled Disinfecting Cap.
U.S. Appl. No. 60/850,438, filed Oct. 10, 2006 entitled Disinfecting Cap.
U.S. Appl. No. 61/195,002, filed Oct. 2, 2008 entitled Site Scrub Brush.
U.S. Appl. No. 11/281,711, filed Nov. 17, 2005 Final Office Action dated Jun. 11, 2010.
U.S. Appl. No. 11/705,805, filed Feb. 12, 2007 Non-Final Office Action mailed Sep. 22, 2009.
U.S. Appl. No. 11/705,805, filed Feb. 12, 2007 Notice of Allowance mailed Jun. 21, 2010.
U.S. Appl. No. 11/732,075, filed Apr. 2, 2007 Non-Final Office Action dated Jul. 27, 2010.
U.S. Appl. No. 12/079,965, filed Mar. 31, 2008 Final Office Action dated Mar. 5, 2010.
U.S. Appl. No. 12/079,965, filed Mar. 31, 2008 Non-Final Office Action dated Oct. 2, 2009.
PCT/US2009/002011 filed Mar. 30, 2009 International Preliminary Report on Patentability dated Oct. 5, 2010.
PCT/US2009/005120 filed Sep. 14, 2009 Preliminary Report on Patentability dated Apr. 5, 2011.
PCT/US2009/005120 filed Sep. 14, 2009 Written Opinion dated Jul. 1, 2010.
PCT/US2010/046096 filed Aug. 20, 2010 Search Report dated Oct. 1, 2010.
PCT/US2010/046096 filed Aug. 20, 2010 Written Opinion dated Oct. 1, 2010.
U.S. Appl. No. 11/732,075 filed Apr. 2, 2007 Non-Final Office Action dated Jan. 4, 2011.
U.S. Appl. No. 11/732,075 filed Apr. 2, 2007 Notice of Allowance dated Apr. 14, 2011.
U.S. Appl. No. 12/079,965 filed Mar. 31, 2008 Non-Final Office Action dated Mar. 9, 2011.

* cited by examiner

SITE SCRUB BRUSH

This application claims the benefit of Provisional Patent Application 61/195,002, filed Oct. 2, 2008.

This invention relates to an improvement of the microbial scrub brush described in pending U.S. patent application Ser. No. 11/732,075 filed Apr. 2, 2007.

As is known various products have been provided in an effort to sterilize the ports of various medical devices. For example, published U.S. Patent Application 2008/0147047 describes a cap that has a threaded interior for threading onto a hub and that has one or more pillows saturated with disinfectant within the interior for engaging the hub. The cap is described as remaining on the hub.

Published U.S. Patent Application 2007/0225660 describes a swab pouch that is to serve as a valve facial swab and a valve cover. As described, the swab pouch has a flattened configuration that can be dilated as by squeezing the pouch between thumb and forefinger. In one embodiment, the swab pouch includes an absorbent inner layer of elastic fabric or non-elastic comprised of absorbent cotton containing a disinfectant. The entire swab pouch may be elastic or the outer layer may be elastic. In one embodiment, the outer layer may be an elastic silicone sleeve, coating or molded component or may be molded with the fabric or molded into the fabric.

Published U.S. Patent Application 2006/0030827 describes a luer cleaner that is described as being sized to receive a luer connector and that has bristles of polypropylene to engage and clean the outer surfaces of the luer connector.

It is an object of this invention to provide a site scrub brush that is relatively inexpensive to manufacture.

It is another object of the invention to provide a site scrub brush that can be manually compressed to enhance the scrubbing effect of the brush on the outer surfaces of a luer.

Briefly, the invention provides a site scrub brush that is formed of a foam material of block-like shape that can receive and retain a solution, such as a cleaning solution or disinfectant, and that is encased by a sealing material, but for one surface, to prevent loss of the solution. The unsealed surface may be covered by a removable cover, such as a foil of aluminum or other suitable material, such that upon removal of the cover, the foam material may be used to swab an instrumentality, such as a luer connector. The sealing material is characterized in being of a nature and/or thickness that is flexible and one that will allow the foam material to be compressed or deformed when squeezed when a connector is inserted into it.

The foam material may be open celled or semi-opened celled and may be molded or extruded or die cut from sheeting.

The sealing material may be polyurethane, polyester or any plastic polymer which is non-permeable in nature and which will act as a barrier preventing any solution from entering or leaving the foam material. The sealing material may be applied to the exposed surfaces of the foam material by being sprayed on or laminated onto the foam material or by dipping of the foam material into the sealing material in order to seal the perimeter and bottom surface of the foam material.

The solution can be a cleaning solution or disinfectant.

The foam material may be shaped and formed into sections, such as described in U.S. patent applications Ser. Nos. 11/732,075 and 12/079,965 and used as described in each patent application, the disclosure of each of which is incorporated herein.

These and other objects and advantages of the invention will become more apparent from the following detailed description taken in conjunction with the accompanying drawings wherein.

Figure 1:
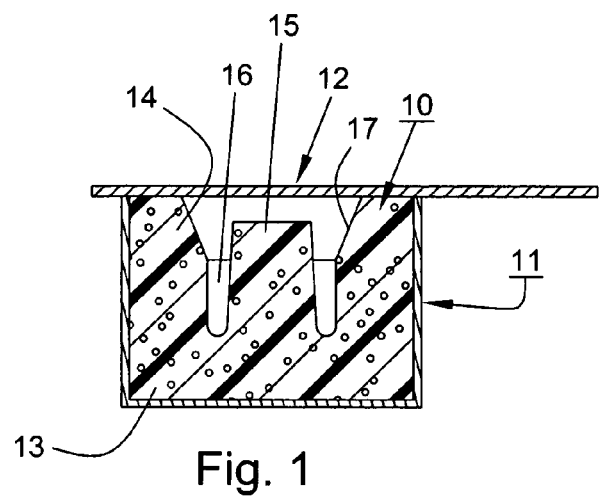
FIG. 1 illustrates a cross-sectional view of a site scrub brush in accordance with the invention.

Referring to FIG. 1, the site scrub brush is fabricated of a foam material 10 of block shape that is surrounded by a thin layer 11 of sealing material. In particular, the foam material is of cylindrical block-like shape and is made of a semi-open celled foam of medium density, such as a semi-closed hydrophilic polyurethane medical grade foam.

The foam material 10 is of a nature to receive a solution, such as a cleaning solution or antibacterial disinfectant solution, and may be used as described in U.S. patent application Ser. Nos. 11/732,075 and 12/079,965.

The sealing material 11 may be polyurethane, polyester or any plastic polymer which is non-permeable in nature and which will act as a barrier preventing any solution from entering or leaving the foam material.

The scrub brush is provided with a removable cover 12 that is secured over an open end of the foam material 10. The cover 12 may be a foil, such as an aluminum foil and is heat sealed to the exposed surface of the foam material 10. The cover (or foil lid) 12 would be peeled away prior to use and will prevent the solution in the foam material 10 from leaking out or drying out.

Alternatively, the cover 12 can be sealed to the thin barrier coating 11 of the sealing material.

In order to fabricate the scrub brush, the foam material 10 is molded or extruded or die cut from sheeting to form a cylindrical block shape. In particular, the foam material 10 is injection molded. Thereafter, the block of foam material 10 is dipped into a sealing material to form a thin layer 11 of the sealing material about the periphery and the bottom of the foam material 10 leaving the top surface exposed.

The thin layer 11 of sealing material is characterized in being of a nature and/or thickness that is flexible and one that will allow the foam material 10 to be compressed or deformed when squeezed when a connector is inserted into it. In particular, the layer 11 of sealing material is of a thickness to seal the peripheral surfaces and bottom of the block of foam material 10 while allowing the resultant scrub brush to be compressed manually under the finger pressure of a user. For example, where the block of foam material has a diameter of 0.75 inches and a height of 0.87 inches, the thickness of the layer is from 0.050 inches to 0.080 inches.

Thereafter, the anti-bacterial disinfectant solution is placed in the foam material 10 and the cover 12 put into place to seal in the solution The molded configuration of the foam material 10 is made to readily accept a medical type connector female luer. The shape configurations can be molded, burned or ground into the foam material 10. As shown, the foam material 10 has a base 13, an annular portion 14 extending upwardly, as viewed, from the base 13 and a central portion 15 extending upwardly from the base 13 in circumferentially spaced concentric relation to the annular portion 14 to define an annular gap 16. The annular portion 15 has a conical inwardly directed surface 17 that provides a narrowing entrance to the gap 16 and the central portion has a flat end 18.

Each of FIGS. 2, 3, 4, 5 and 6, wherein like reference characters indicate like parts as above, displays different configurations in which the foam material 10 can be molded or extruded to form different shapes for various connectors.

Figure 2:
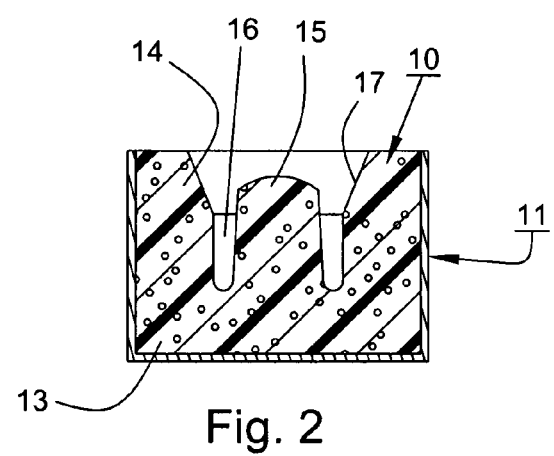
FIG. 2 illustrates a cross-sectional view of a modified site scrub brush in accordance with the invention.

Referring to FIG. 2, the central portion 15 of the scrub brush is made with a rounded end 19.

Figure 3:
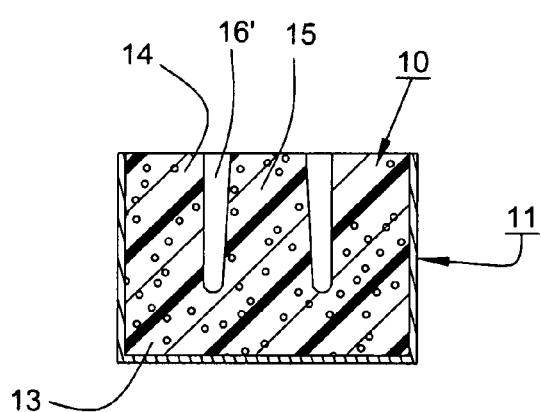
FIG. 3 illustrates a cross-sectional view of a modified site scrub brush in accordance with the invention having a conically tapered central section.

Referring to FIG. 3, the scrub brush has a gap 16' that extends the full depth of the central portion 14 without a conical entrance portion as in FIG. 1.

Figure 4:
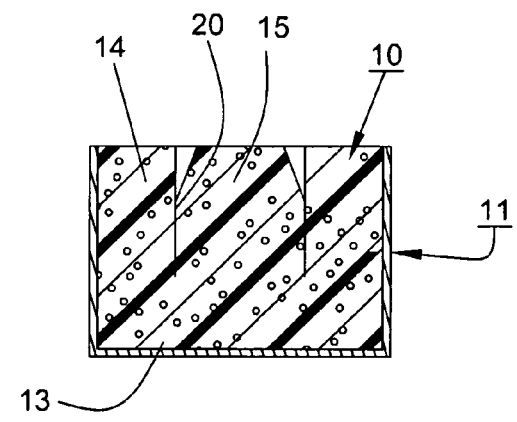
FIG. 4 illustrates a cross-sectional view of a modified site scrub brush in accordance with the invention having a conically tapered central portion defining an entrance between the annular portion and central portion.

Referring to FIG. 4, the scrub brush has an annular slit 20 that separates the annular portion 14 from the central portion 15 so that the two portions are contiguous to each other. In addition, the central portion 15 is tapered at the end.

Figure 5:
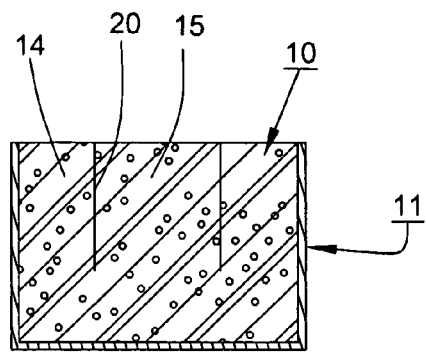
FIG. 5 illustrates a cross-sectional view of a modified site scrub brush in accordance with the invention having an annular slit to define an annular portion and a central portion.
Figure 6:
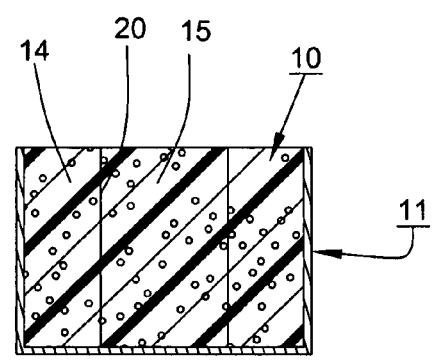
FIG. 6 illustrates a view similar to FIG. 5 with a slit extending throughout the length of an annular portion and a central portion.
Figure 7:
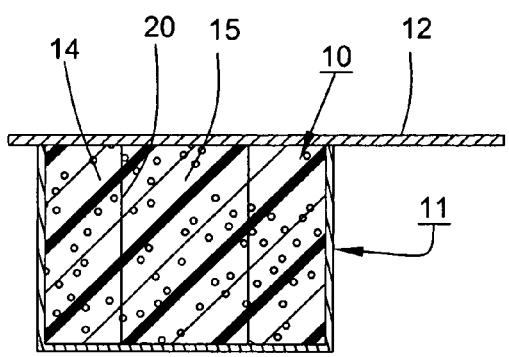
FIG. 7 illustrates a view similar to FIG. 6 with a cover in place.

As indicated in FIG. 5, the annular slit separating the annular portion of the foam material 10 from the central portion may extend half-way into the foam material or, as indicated in FIGS. 6 and 7, the annular slit may extend completely through the foam material 10.

The construction of the scrub brush allows the scrub brush to be handled as a self contained individually sterile device. For example, since the surfaces of the foam material 10 are closed by the layer 11 of sealing material and the cover 12, the foam material can be maintained in a sterile condition until ready for use.

The outer barrier 11 and the foil lid 12 will keep the contents of the foam area sterile. The site scrub brush can be supplied in cases of 50 to 100 units. If the unit is dispensed in a sealed pouch with one or more units, the individual units remain sterile on their own merit.

In use, in order to clean a luer, the cover 12 is removed from the scrub brush and the luer inserted into the foam material 10. In this respect, the luer is inserted coaxially between the annular portion 14 and the central portion 15 such that the outer surfaces of the luer engage with the inner surfaces of the annular portion 14 and the inner surfaces of the luer engage with the outer surfaces of the central portion. Thereafter, the scrub brush is rotated about the luer to scrub the inside and outside surfaces of the luer via the foam material. During this time, debris from the luer is absorbed by the foam material. Due to the flexible nature of the layer 11 of sealing material and the compressibility of the foam material 10, the use may impose a compressive force on the scrub brush during rotation on the luer to enhance the scrubbing action of the annular portion of the foam material on the outside surfaces of the luer.

The invention thus provides a site scrub brush that is relatively inexpensive to manufacture and one that can be manually compressed to enhance the scrubbing effect of the brush on the outer surfaces of a luer.

What is claimed is:

1. A site scrub brush, comprising:
   a foam material of block-like shape for receiving and retaining a solution;
   a sealing material encasing said foam material but for one surface thereof to prevent loss of the solution, wherein said sealing material is a coating on said foam material; and
   a removable cover covering said one surface, wherein said foam material includes an annular portion for enveloping an outer surface of a female luer and a central portion concentrically within said annular portion for insertion within a central passage of the female luer; the central portion has an outer conical surface.

2. A site scrub brush as set forth in claim 1, wherein said cover is a foil of aluminum.

3. A site scrub brush as set forth in claim 1, wherein said sealing material is characterized in being flexible to a degree sufficient to allow said foam material to be deformed in response to insertion of a connector thereinto.

4. A site scrub brush as set forth in claim 3, wherein said sealing material is non-permeable.

5. A site scrub brush as set forth in claim 3, wherein said sealing material is made of a material selected from the group consisting of polyurethane and polyester.

6. A site scrub brush as set forth in claim 1, wherein said foam material is of cylindrical shape about a longitudinal axis.

7. A site scrub brush as set forth in claim 1, wherein said central portion is circumferentially spaced from said annular portion.

8. A site scrub brush as set forth in claim 1, wherein said central portion is circumferentially contiguous to said annular portion.

9. A site scrub brush as set forth in claim 1, further comprising an anti-bacterial disinfectant solution impregnated in said foam material for disinfecting the outside surface and the interior of a female luer.

10. A site scrub brush as set forth in claim 1, wherein said foam material is a semi-closed hydrophilic polyurethane medical grade foam.

11. A site scrub brush as set forth in claim 1, wherein the annular portion comprises a rounded end.

12. A site scrub brush, comprising:
    a foam material of block-like shape for receiving and retaining a solution;
    a sealing material encasing the foam material but for one surface thereof to prevent loss of the solution, the sealing material laminated on the foam material; and
    a removable cover covering the one surface, wherein the foam material comprises a central portion circumferentially within and concentric with an annular portion.

13. A site scrub brush as set forth in claim 12, wherein the central portion is radially separated from the annular portion by a circumferential slit.

14. A site scrub brush as set forth in claim 13, wherein the circumferential slit extends along an entire longitudinal length of the foam material.

15. A site scrub brush as set forth in claim 13, wherein the annular portion and central portion are coextensive along a longitudinal length of the site scrub brush.

16. A site scrub brush as set forth in claim 13, wherein an end of the central portion is longitudinally recessed within the site scrub brush from a corresponding end of the annular portion.

* * * * *